United States Patent [19]
Gubernick et al.

[11] Patent Number: 6,066,327
[45] Date of Patent: *May 23, 2000

[54] ANTIOXIDANT MIXTURE

[75] Inventors: Joseph Gubernick, New York; Kenneth D. Marenus, Dix Hills; Edward Pelle, Valley Stream, all of N.Y.; Lieve Declercq, Ekeren, Belgium; Daniel H. Maes, Huntington, N.Y.

[73] Assignee: Color Access, Inc., Melville, N.Y.

[*] Notice: This patent is subject to a terminal disclaimer.

[21] Appl. No.: 09/014,232

[22] Filed: Jan. 27, 1998

Related U.S. Application Data

[63] Continuation-in-part of application No. 08/992,128, Dec. 17, 1997.

[51] Int. Cl.$^7$ .............................. A61K 6/00; A61K 7/42
[52] U.S. Cl. ..................... 424/401; 424/59; 424/69; 424/63
[58] Field of Search ........................ 424/401, 63, 448, 424/59, 69

[56] References Cited

U.S. PATENT DOCUMENTS

| | | |
|---|---|---|
| 3,903,317 | 9/1975 | Cort . |
| 4,003,919 | 1/1977 | Scott et al. . |
| 4,018,799 | 4/1977 | Scott et al. . |
| 4,026,907 | 5/1977 | Scott et al. . |
| 5,230,916 | 7/1993 | Chang et al. ............................ 424/330 |
| 5,376,361 | 12/1994 | Perricone .................................. 424/59 |
| 5,616,332 | 4/1997 | Herstein .................................. 424/401 |
| 5,658,556 | 8/1997 | Gers-Barlag et al. ..................... 424/63 |
| 5,811,083 | 9/1998 | Pelle et al. ................................. 424/59 |

FOREIGN PATENT DOCUMENTS

| | | |
|---|---|---|
| 88/03015 | 5/1988 | WIPO . |

OTHER PUBLICATIONS

Packer,L.;C.A.Rice–Evans and R.H. Bufdon: (Eds.), Free Radical Damage and its Control, 1994 Elsevier Science B.V.,9:pp. 239–255, Ultraviolet Radiation (UVA,UVB) and Skin Antioxidants.

Miyachi, et al., Clinical and Experimental Dermatology (1983) 8:pp. 305–310, Sunburn Cell Formation is Prevented by Scavenging Oxygen Intermediates.

Khettab, et al., Biochimie 70:pp. 1709–1713, 1988 Photoprotective Effect of Vitamins A and E on Polyamine and Oxygenated Free Radical Metabolism in Hairless Mouse Epidermis.

E. Law & A.J. Lewis, Br. J. Pharmacol. 59:pp. 591–597, 1977, The Effect of Systemically and Topically Applied Drugs on Ultraviolet–Induced Erythema in the Rat.

Bissett, et al., Photodermatol. Photoimmunol. Photomed. 7: pp. 56–62, 1990, Photoprotective Effect of Superoxide–Scavenging Antioxidants Against Ultraviolet Radiation–Induced Chronic Skin Damage in the Hairless Mouse.

*Primary Examiner*—Thurman K. Page
*Assistant Examiner*—Susan Tran
*Attorney, Agent, or Firm*—Kenyon & Kenyon

[57] ABSTRACT

The present invention relates to cosmetic or pharmaceutical compositions for topical application to the skin, the compositions comprising effective amounts of at least one of each of the antioxidants selected from the group consisting of (a) tocopherol and derivatives thereof, (b) ascorbic acid and derivatives thereof, (c) a butylated phenol, (d) a rosemary extract, and (e)ubiquinone and derivatives thereof. The compositions are useful in treating and preventing the symptoms of photoaging.

16 Claims, No Drawings

ANTIOXIDANT MIXTURE

RELATED APPLICATIONS

This application a continuation-in-part of U.S. Ser. No. 08/992,128, filed Dec. 17, 1997, the contents of which are incorporated herein by reference.

FIELD OF THE INVENTION

The invention relates to cosmetic and pharmaceutical compositions for topical application to the skin. More specifically, the invention relates to compositions useful in preventing and treating the signs of extrinsic aging in the skin.

BACKGROUND OF THE INVENTION

It has now long been recognized that there is a cause-and-effect relationship between prolonged and/or repeated exposure to UV light and premature aging of the skin. In general terms, excessive exposure to the sun contributes substantially to premature decline in the quality and quantity of elastin and collagen in the skin, as well as hypertrophy of the epidermis. These changes are manifested externally by typical signs of aging, such as deep lines and wrinkles, loss of elasticity, skin dryness and unevenness, and increased frequency of blotches, pigmented spots, and benign as well as malignant neoplasms.

It has also been proposed that to a large extent the damage done is due to the generation of free radical species on the skin by UV radiation. Free radicals, if uncontrolled, may rapidly, and randomly, react with molecules in their vicinity, giving rise to toxic products that can interfere with the body's normal physiological processes. The cumulative effects of these reactions can, and probably always eventually do, overwhelm the body's normal repair mechanisms. Free radical reactions are widely considered to have a major contributory effect on the natural aging process.

It has been recognized in recent years that the presence of oxygen radicals on the skin is probably responsible for a number of the undesirable effects of exposure to the sun. For example, the aging phenomenon generally observed throughout the body is frequently observed prematurely on the skin as a result of photoaging, which accelerates the process of deterioration of elastin and collagen, among other effects. There is also an increased risk of skin cancer of all types. In response to this need, the skin care industry has continued to seek new and more effective means for combating the these processes. Antioxidants in general have not, to date, been shown to have an in vivo protective effect on human skin against a routine, non-acute exposure to sun, and there has been much skepticism as to whether antioxidants can really be expected to have measurable effect on the aging process. There thus continues to be a need for a composition which is effective in the treatment, prevention, or even reversal, of the symptoms of photoaging.

SUMMARY OF THE INVENTION

The invention relates to cosmetic or pharmaceutical compositions for topical application to the skin, the composition comprising a least one of each of the antioxidants selected from the group consisting of (a) tocopherol and derivatives thereof, (b) ascorbic acid and derivatives thereof,(c) a butylated phenol, (d)a rosemary extract, and (e)ubiquinone or a derivative thereof. The composition is useful in the treatment and prevention of photoaging, i.e., that damage to the skin which occurs as a result of repeated exposure to the sun.

DETAILED DESCRIPTION OF THE INVENTION

As noted above, it has definitely been recognized that various oxygen free radicals and reactive species are implicated in the damage resulting from prolonged exposure to UV radiation and other environmental insults. Various types of antioxidants have been tested experimentally to determine if they may have an ameliorating effect on UV-induced damage(Packer, L. in *Free Radical Damage and its Control*, 9: 239–255, 1994, Rice-Evans & Burton, eds., Elsevier Science B. V.; Miyachi et al. *Clin. Exp. Dermatol.* 8: 305–310, 1983; Khettab et al., *Biochimie* 70: 1709–1713, 1988; Law and Lewis, *Br. J. Pharmacol.* 59: 591–597, 1977; Bissett et al., *Photodermatol. Photoimmunol. Photomed.* 7: 56–62, 1990). However, to date, such studies have focused on the effect of antioxidants on damage caused by acute UV exposure, and primarily on animal models. There is no previous evidence to suggest that antioxidants can have any protective effect in vivo against long-term, regular exposure to the sun.

The combination of antioxidants of the present compositions provide a protective effect against lipid peroxidation on the skin surface. High lipid peroxide levels are recognized as an indicator of an acute event of oxidative stress. The combination can also be used to protect against the development of lines and wrinkles, preventing the worsening of existing wrinkles, and to a lesser extent, even promoting some regression in existing lines and wrinkles. The combination also provides a protective effect against loss of elasticity and skin thickness which characterizes photoaging. The protective effects are particularly useful for treatment of chronically sun-exposed skin.

The components of the combination are known antioxidants that are either commercially available or readily prepared. All components are used in antioxidant-effective amounts, these amounts varying depending upon the identity of the compound and its potency. A first component of the combination is Vitamin E or a homologue, analog or derivative thereof. The principle active component of Vitamin E is tocopherol, particularly α-tocopherol; however, any Vitamin E or tocopherol derivative may be employed. Examples of useful derivatives are esters, for example, tocopherol acetate, tocopherol linoleate, tocopherol nicotinate, tocopherol sorbate, or tocopherol succinate; polyethylene glycol ethers of tocopherol, such as tocophereth-5, tocophereth-10, tocophereth-12, tocophereth-18 or tocophereth-50 and 6-hydroxychroman homologues, (such as are described in U.S. Pat. Nos. 4,003,919; 4,018,799; 4,026,907 and 3,903, 317)particularly 6-hydroxy-2,5,7,8-tetramethylchroman-2-chroman-2-carboxylic acid, commercially available as Trolox®-C(Cort et al., *JAOCS* 52: 174, 1975) and Troloxyl-amino acids(Taylor et al., *JAOCS:* 622, 1981).

The tocopherol derivative may also be a tocopherol-cysteamine having the formula:

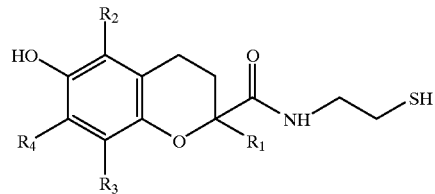

or cosmetically or pharmaceutically acceptable salts thereof, wherein $R_1$, $R_2$, $R_3$, and $R_4$ may be the same or different, and are independently selected from the group consisting of hydrogen, $C_1$–$C_{18}$ alkyl, substituted $C_1$–$C_{18}$ alkyl, $C_1$–$C_{18}$ alkoxy, substituted $C_1$–$C_{18}$ alkoxy, $C_1$–$C_{18}$ alkenyl, substituted $C_1$–$C_{18}$ alkenyl, $C_1$–$C_{18}$ alkynyl, and substituted $C_1$–$C_{18}$ alkynyl. The alkyl, alkenyl, alkoxy and alkynyl groups may be straight- or branched chain, and substituted with halogen, OH, SH, $NH_2$, $NO_2$, and the like. A preferred compound is one in which $R_1$–$R_4$ are each $C_1$–$C_4$, and more preferably each is methyl. Other preferred compounds are those in which $R_1$ is methyl, and $R_3$, $R_3$, and $R_4$ are the same or different, and may be H, OH or $C_1$–$C_4$ alkyl, $C_1$–$C_4$ alkoxy, Cl, Br, F, $NO_2$, $NH_2$, or $N(R_5)_2$, wherein $R_5$ is $C_1$–$C_4$ alkyl. The tocopherol-cysteamine compounds can be made using readily available starting materials according to the following scheme:

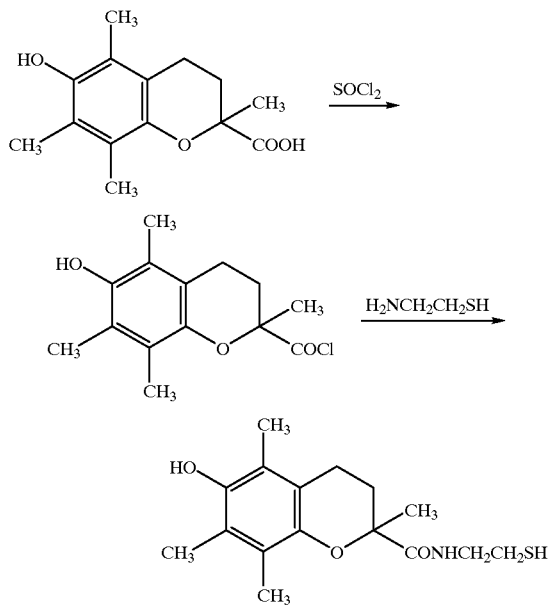

The amount of Vitamin E-related component used in the composition will vary depending upon the potency of the chosen component, but will generally be in the range of from about 0.01–20% by weight of the total composition. In one preferred embodiment, there is more than one Vitamin E component in the mixture; particularly preferred is a mixture containing both α-tocopherol or tocopheryl acetate and tocopherol cysteamine.

A second component is Vitamin C(ascorbic acid) or a homologue, analog or derivative thereof. The derivatives of Vitamin C which may be used are, for example, ascorbyl esters of fatty acids, such as ascorbyl palmitate, ascorbyl dipalmitate, ascorbyl dimethylsilanol palmitate, and ascorbyl stearate; metal or metal phosphate salts, such as magnesium, sodium, or potassium ascorbyl phosphate, or magnesium, sodium or potassium ascorbate. This component is typically present in an amount of from about 0.01–20% by weight, more preferably from 1–10%.

A third component is a butylated phenol, or a salt thereof. Examples include t-butyl hydroquinone, di-t-butyl hydroquinone, and BHT. Particularly preferred for use in the composition of the invention is BHT. This component is preferably used in an amount of from about 0.01–1%, preferably 0.01–0.5%, by weight of the total composition.

A fourth component is a ubiquinone(ubidecarenone) or derivative thereof. Ubiquinone is a naturally occurring hydrogen carrier in the respiratory chain(coenzyme Q); structurally, it is a 2,3-dimethoxy-5-methyl-1,4-benzoquinone with a multiprenyl side chain, the number of isoprene units varying depending upon the organism. The composition may contain any ubiquinone, or combinations thereof, or may also be represented as the reduced form, ubiquinol. Other ubiquinone derivatives are described, for example, in WO 8803015. The ubiquinone component is preferably employed in an amount of from about 0.01–1%, preferably 0.01–0.5% by weight of the total composition.

A final component of the combination is a rosemary extract, by which is meant the whole extract, or an active fraction thereof. Preferably the extract is an oil-soluble extract. Such rosemary extracts are commercially available from a variety of manufacturers. The preferred antioxidant fraction of the extract are primarily in the dehydroabeitic acid class of diterpenes. Among the specifically identified active ingredients of the extract are carnosol, carnosic acid and rosmanol. However, there are other unidentified components of the extract which also possess antioxidant activity, and these may also be used in the composition. The preferred extract is one which contains from about 1–5% carnosic acid, from about 2–7% carnosol, and from about 0.1–1% rosmanol; such an extract is commercially available under the tradename Stabex™, from SKW Chemicals. An extract of this type can be used in an amount of from about 0.0001 to about 1%, preferably about 0.005–0.5%, more preferably from about 0.01–0.1%, by weight of the total composition. However, it will be understood that the composition may also simply use one or more of the individual components of the useful extracts.

In a preferred embodiment, the composition may also comprise additional cosmetically acceptable antioxidant components. Examples of other antioxidant components which may be incorporated with the novel combination are green tea extract, beta carotene, gamma oryzanol, proanthocyanidins, such as are found in grapeseed extract or pine bark extract, or any mixture thereof.

For topical application, the antioxidant mixture can be combined with a cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pa., 1990. The carrier may be in any form appropriate to the mode of delivery, for example, solutions, colloidal dispersions, emulsions(oil-in-water or water-in-oil), suspensions, creams, lotions, gels, foams, mousses, sprays and the like.

The formulation, in addition to the carrier and the antioxidant mixture, also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like. As will be apparent, the composition can be a therapeutic product, the antioxidants being the sole actives, or in combination with other actives. However, the composition can also be a makeup product, for example, a lipstick, foundation, concealer, bronzer, blush, eyeshadow and the like.

In one preferred embodiment, the composition also contains a sunscreen. The combination may be with any sunscreen. Examples of sunscreens useful in the compositions include, but are not limited to, inorganic sunscreens such as titanium and zinc oxides, or organic sunscreens such as para-amino benzoic acid(PABA)and its esters, benzophenones, phenyl or homomenthyl salicylates, and cinnamates. In such a composition, the sunscreen of choice is employed in an amount consistent with the established use of that sunscreen.

The compositions of the invention can be applied on an as-needed basis, for example, applied to the skin before anticipated prolonged sun exposure, or during or after such exposure. However, as the best results are achieved after regular application over a period of time, a preferred method of obtaining the benefits of the composition is via chronic topical application of a safe and effective amount of a composition containing the mixture, to prevent development of skin damage which may result from even routine exposure to UV light or other environmental insults which may result in the generation of reactive oxygen species, or to prevent worsening of or to reverse existing damage. It is suggested as an example that topical application of the composition, in an amount of from about 0.1 $\mu$g/cm$^2$ to 2 mg/cm$^2$ of exposed skin, be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years, thereby resulting in the treatment or prevention of the external signs of photoaging. It will be recognized by those skilled in the art that the treatment regimen employed can be varied depending upon the user's level of exposure to noxious stimuli; a chronically sun-exposed individual may benefit from more frequent applications than will be necessary for an individual who avoids the sun.

EXAMPLES

I. A composition of the invention is prepared as follows, using conventional mixing techniques:

|      | Material                  | Weight % |
|------|---------------------------|----------|
| I.   | deionized water           | 43.78    |
|      | 1,3-butylene glycol       | 4.00     |
|      | polysorbate 60            | 1.50     |
|      | methyl paraben            | 0.20     |
|      | PPG-20 methyl glucose ether | 0.40   |
|      | trisodium EDTA            | 0.10     |
|      | carbomer                  | 18.50    |
| II.  | octyl methoxycinnamate    | 5.00     |
|      | beta carotene             | 0.02     |
|      | phenyl trimethicone       | 4.00     |
|      | myristyl lactate          | 4.50     |
|      | stearyl alcohol           | 1.00     |
|      | sorbitan stearate         | 2.00     |
|      | stearic acid              | 1.20     |
|      | BHT                       | 0.15     |
|      | gamma oryzanol            | 0.10     |
|      | titanium dioxide          | 2.00     |
| III. | dicaprylyl maleate        | 0.30     |
|      | ubiquinone                | 0.10     |

-continued

|      | Material                    | Weight % |
|------|-----------------------------|----------|
| IV.  | tocopheryl acetate          | 2.00     |
| V.   | cyclomethicone              | 5.00     |
| VI.  | deionized water             | 2.00     |
|      | 1,3 butylene glycol         | 2.00     |
|      | citric acid                 | 0.10     |
|      | magnesium ascorbyl phosphate | 0.20    |
|      | carnosol/rosmanol extract   | 0.10     |
|      | green tea extract           | 0.25     |

What we claim is:

1. A cosmetic or pharmaceutical composition for topical application to the skin which comprises (a)from about 0.01 to about 20% of tocopherol and/or a tocopherol derivative; (b)from about 0.01 to about 20% of ascorbic acid and/or a derivative thereof; (c) from about 0.01 to about 0.5% of a butylated phenol; (d) from about 0.01 to about 1% ubiquinone and (e) from about 0.0001 to about 1% of a rosemary extract, the extract comprising from about 1 to about 5% carnosic acid, from about 2 to about 7% carnosol, and from about 0.1 to about 1% rosmanol.

2. The composition of claim 1 which comprises tocopheryl acetate and tocopherol cysteamine, and an ascorbyl phosphate.

3. The composition of claim 1 which also comprises at least one additional antioxidant selected from the group consisting of green tea extract, beta carotene, gamma oryzanol, a proanthocyanidin; and any mixture thereof.

4. A method for treating or preventing the symptoms of photoaging on the skin comprising applying to the skin a composition according to claim 1.

5. The method of claim 4 in which the composition is applied about once or twice daily.

6. The method of claim 5 in which the composition is applied over a period of from about three months to about twenty years.

7. A method for treating, preventing, or reducing lines and wrinkles on the skin which comprises applying to the skin a composition according to claim 1.

8. A method for treating or preventing loss of elasticity in the skin which comprises applying to the skin a composition according to claim 1.

9. A method for treating or preventing skin thinning which comprises applying to the skin a composition according to claim 1.

10. A method for treating or preventing skin dryness which comprises applying to the skin a composition according to claim 1.

11. The composition of claim 1 which comprises a tocopherol derivative.

12. The composition of claim 1 in which the ascorbic acid derivative is an ascorbyl phosphate.

13. The composition of claim 1 in which the butylated phenol is BHT.

14. The composition of claim 1 which contains tocopheryl acetate, tocopherol cysteamine, and an ascorbyl phosphate.

15. The composition of claim 14 which comprises magnesium ascorbyl phosphate.

16. The composition of claim 11 which comprises (a)α-tocopherol or tocopheryl acetate, and tocopherol cysteamine, (b) an ascorbyl phosphate, c) BHT, (d)the rosemary extract, and (e)ubiquinone.

* * * * *